United States Patent
Selz et al.

(10) Patent No.: US 9,867,948 B2
(45) Date of Patent: Jan. 16, 2018

(54) ADMINISTERING DEVICE WITH PRIMING FUNCTION

(75) Inventors: Anjan Selz, Bern (CH); Manfred Rettenbacher, Meisterschwanden (CH); Fritz Kirchhofer, Sumiwald (CH)

(73) Assignee: TecPharma Licensing AG, Burgdorf (CH)

( * ) Notice: Subject to any disclaimer, the term of this patent is extended or adjusted under 35 U.S.C. 154(b) by 1335 days.

(21) Appl. No.: 13/335,275

(22) Filed: Dec. 22, 2011

(65) Prior Publication Data
US 2012/0203184 A1 Aug. 9, 2012

Related U.S. Application Data

(63) Continuation of application No. PCT/EP2009/057934, filed on Jun. 24, 2009.

(51) Int. Cl.
*A61M 5/31* (2006.01)
*A61M 5/315* (2006.01)
*A61M 5/24* (2006.01)
*A61M 5/50* (2006.01)

(52) U.S. Cl.
CPC ...... *A61M 5/31553* (2013.01); *A61M 5/3146* (2013.01); *A61M 5/3156* (2013.01); *A61M 5/3158* (2013.01); *A61M 5/2466* (2013.01); *A61M 5/3157* (2013.01); *A61M 5/31591* (2013.01); *A61M 5/502* (2013.01); *A61M 2005/3118* (2013.01)

(58) Field of Classification Search
CPC .............. A61M 5/2448; A61M 5/3146; A61M 5/31553; A61M 5/3156; A61M 5/3158; A61M 5/31593; A61M 5/31595
See application file for complete search history.

(56) References Cited

U.S. PATENT DOCUMENTS

| | | | | |
|---|---|---|---|---|
| 5,092,842 A | * | 3/1992 | Bechtold | A61M 5/20 604/135 |
| 8,961,463 B2 | * | 2/2015 | Edhouse | A61M 5/20 604/135 |
| 2003/0158523 A1 | | 8/2003 | Hjertman et al. | |
| 2005/0137571 A1 | * | 6/2005 | Hommann | A61M 5/31553 604/500 |

FOREIGN PATENT DOCUMENTS

| | | |
|---|---|---|
| EP | 0 373 321 | 6/1990 |
| EP | 0 927 058 | 7/1999 |
| EP | 1 101 505 | 5/2001 |
| EP | 1 188 444 | 3/2002 |
| WO | WO 1997/001362 | 1/1997 |
| WO | WO 2000/062839 | 10/2000 |
| WO | WO 2005/039676 | 5/2005 |

* cited by examiner

*Primary Examiner* — Scott Medway
(74) *Attorney, Agent, or Firm* — Dorsey & Whitney LLP (57) ABSTRACT

An administering device, e.g. an injection device, includes a housing, a reservoir for a drug, the reservoir formed or accommodated by the housing, a dosing member which can perform a dosing movement relative to the housing for setting a dosage of the drug to be administered and a conveying member for delivering the dosage set, wherein the dosing member is blocked or locked in the direction of the dosing movement in a releasable dosing blocking engagement in an initial state of the administering device and released from the block at the end of a priming movement of the conveying member.

23 Claims, 4 Drawing Sheets

ADMINISTERING DEVICE WITH PRIMING FUNCTION

CROSS-REFERENCE TO RELATED APPLICATIONS

This application is a Continuation of International Patent Application No. PCT/EP2009/057934 filed Jun. 24, 2009, the contents of which are hereby incorporated by reference.

BACKGROUND

The present invention relates to devices for administering, injecting, infusing, delivering or dispensing a substance, and to methods of making and using such devices. More particularly, it relates to an administering device for a liquid drug which can be a liquid formulation which contains FSH or an FSH variant. For the purposes of the present invention, not only liquids in the narrower sense but also pasty and gelatinous drugs are to be regarded as liquid drugs, as long as such drugs can be conveyed in a way comparable to a liquid. In some embodiments, an administering device in accordance with the present invention is an injection device for administering a substance by an infusing injection needle, e.g. for a subcutaneous injection, but it can in principle also be an injection device for needle-less administering or an inhalation device. In some embodiments, an injection device in accordance with the present invention takes the form of a so-called injection pen.

Modern injection pens enable a drug to be precisely dosed, even individually or personally by a patient. The increased flexibility due to the freely selectable dosage enables the device to be used in therapies in which the patients administer a drug to themselves—so-called self-administering. Self-administering in particular demands a high level of operational security and operational convenience. The devices should inherently prevent operational errors. One source of error is air trapped in the drug reservoir. If this air is not removed before administering, there is a danger that the drug to be administered will not be administered in the dosage set but rather together with the trapped air in accordance with the dosage set. The drug reservoir is therefore vented before administering, a process which is generally known as "priming". In the majority of devices, priming is left to the instinct of the patient, who for this purpose sets a small dosage on a dosing member, holds the device with the needle pointing up, and delivers the priming volume set into the air by activating the device. Other devices, for example a device known from EP 0 927 058 A1, are specially equipped with priming mechanisms which may entail a highly complex design and therefore significantly increased costs.

Because of the need to reduce costs, more and more therapies are being given over to self-administering. One example is stimulating the ovaries and consequently, by fertilizing the stimulated egg cells, pregnancy using hormone treatment. Thus, for example, EP 1 188 444 B1 describes liquid formulations based on FSH (follicle stimulating hormone) and FSH variants. To also be able to administer FSH and FSH variants by self-administering, the liquid formulation—the drug—is preserved. A preservative is added to the active agent FSH or an FSH variant—in a liquid solution. If unpreserved, there would be a danger of the drug containing the FSH or an FSH variant becoming contaminated, such that it would have to be administered within a few hours, and optimally immediately, after contact with air. In most cases, therefore, the drug is dispensed in a preserved form in larger containers, from which the patients can charge their administering device, i.e. fill its reservoir with the preserved drug. Alternatively, the patient is provided with two containers, one with an unpreserved formulation and the other with the preservative, such that the patient can personally mix the preserved drug and store it for a longer period of time in its then preserved state. In addition to the preserving effect, the preservative has, if any, a negative effect on the stability of the active agent (FSH or FSH variants) and also increases the price of the prepared, preserved drug. Charging or mixing the administering device from a larger, sterilely sealed container which contains a preserved or unpreserved formulation is awkward and requires that the dosage to be administered be charged exactly.

SUMMARY

Any reference to "the invention" or "the present invention" in this application shall not be construed as a generalization, limitation or characterization of any subject matter disclosed herein and shall not be considered to be an element or limitation of the appended claims except if and/or where explicitly recited in a claim(s).

It is an object of the present invention to provide an administering device which can be used in therapies involving self-administering, which is simple in design and inexpensive, but still reliably ensures that precisely the required dosage is administered, together with a level of operational convenience which is adequate for self-administering. The device should be suitable for administering an unpreserved liquid formulation which contains FSH or an FSH variant.

In one embodiment, the present invention comprises an administering device, e.g. an injection device, comprising a housing, a reservoir for a drug, the reservoir formed or accommodated by the housing, a dosing member which can perform a dosing movement relative to the housing for setting a dosage of the drug to be administered and a conveying member for performing a priming movement and for delivering the dosage set, wherein the dosing movement is prevented in an initial state of the administering device and allowed at the end of the priming movement.

In some embodiments, the present invention is an administering device which comprises a housing, a reservoir for a liquid drug, a dosing member for setting a dosage of the drug to be administered, and a conveying means comprising a conveying member for delivering the dosage set. The housing can directly form the reservoir if, for example, a syringe forms the housing or a part of the housing. The reservoir can however also be a container, e.g. an ampoule, vial or carpoule, which is accommodated in the housing. The dosing member can be moved relative to the housing to set the dosage. The movement which the dosing member performs when selecting the dosage, and the mobility which it has relative to the housing for selecting the dosage, may be referred to and/or thought of as the dosing movement and the dosing mobility. The conveying means can be formed as a linear stroke conveying means and correspondingly comprise an axially movable piston which sterilely seals the reservoir at one end and, in an advancing movement, displaces and thus delivers the drug through an outlet of the reservoir. The conveying member mentioned can form the piston. In some embodiments, the conveying member forms a piston rod which acts on the piston, or the conveying member is arranged further up the conveying line but ultimately outputs onto the piston or another conveying member which acts directly on the drug situated in the reservoir. In some preferred embodiments, the conveying member is a conveying member which performs an advancing movement, which movement may be referred to and/or thought of as the delivery movement.

In some preferred embodiments, an administering device in accord with the present invention consists of the components mentioned above, namely the housing, the reservoir, the conveying member and the dosing member, wherein the conveying member and the dosing member are formed together in one piece or alternatively are formed by two parts which are formed separately and connected to each other such that they are fixed and cannot be moved. If formed in a single piece or joined to a structure which can only be moved as a whole, the functional components "dosing member" and "conveying member" may be referred to and/or thought of as the "dosing and conveying member." As mentioned, the reservoir can be formed by the housing itself, which in such embodiments can be formed as a syringe or can comprise a syringe-like housing part. If, as is preferred in some embodiments, the conveying means comprises a piston, then the piston is already inherently arranged in the reservoir, i.e. arranged in the reservoir by the manufacturer and not by the patient. In some embodiments, the piston is a simple stopper with no piston rod. The piston rod or other comparable conveying member only acts in an axial pressing contact against the rear side of the piston during conveying to move it in the advancing direction within the reservoir. Alternatively, a piston rod can be connected in a positive fit to a simple stopper, which does not inherently comprise a piston rod, when assembling the device. The device is assembled by the manufacturer of the device or the manufacturer of the drug, such that the patient or also a physician who may be supervising the therapy is provided with the prepared device comprising the reservoir which is already filled with the drug, and merely has to perform the administering itself.

In accordance with the present invention, the dosing member is blocked, or locked or prevented from moving, in the direction of the dosing movement in a releasable dosing blocking or locking engagement, in an initial state of the administering device in which the patient is provided with the device, and is released from the block or lock at the end of a priming movement of the conveying member which serves to vent the reservoir, automatically without any additional effort by the patient, who only has to initiate the priming movement. The conveying member performs the priming movement in a direction transverse to the direction of the dosing movement. The direction of the priming movement of the conveying member is also the advancing direction during the delivery movement. The advancing direction may also be referred to and/or thought of as the axial direction; it extends along a central longitudinal axis of the device.

In one embodiment, an administering device in accordance with the invention features a sequence controller which provides, forces and/or controls an administering sequence. Due to the dosing blocking engagement, the reservoir has to be vented before the dosage is set. In one of the preferred embodiments, the sequence controller is also realized such that the dosage has to be set before the drug is delivered, such that administering can proceed, in some preferred embodiments only proceed, in a priming-dosing-delivery sequence.

In some embodiments, the dosing member can be moved transverse to the advancing direction to set the dosage. A rotational dosing mobility about a rotational axis, which can coincide with a central longitudinal axis of the device, may be preferred in some embodiments. In such embodiments, the dosing member in the dosing blocking engagement abuts against a rotational abutment in the circumferential direction about the rotational axis, i.e. presses against the rotational abutment in a tangential direction in relation to the rotational axis when an attempt is made to set a dosage. The dosing member and the rotational axis can be rotationally moved back and forth and is in a dosing blocking engagement in relation to both rotational directions, i.e. presses against a rotational abutment in each of the two rotational directions when an attempt is made to rotate it.

In some embodiments, the dosing member can be moved in the advancing direction of the conveying member along the rotational abutment, out of the dosing blocking engagement. In some preferred embodiments, it is automatically moved out of the dosing blocking or locked engagement along the rotational abutment or the left-hand and right-hand rotational abutment during the priming movement of the conveying member and/or by the priming movement. In accordance with some preferred embodiments, the dosing member is coupled to the conveying member such that it is slaved in the priming movement of the conveying member. The dosing member and the conveying member can be formed together in one piece or can be formed as separate parts and joined fixedly to each other.

The present invention also comprises securely administering liquid drugs in which the active agent(s) is/are in danger of contamination by air, such as formulations which contain FSH or an FSH variant as their essential active agent, wherein a particular concern is to avoid the use of preservatives, not least in view of negative effects on the respective active agent or agents, but also in view of the additional costs which arise by adding preservatives. In accordance with the present invention, the reservoir comprising the unpreserved liquid drug is dispensed to the patient, e.g. in the form of a complete administering device or a part of the device which can be assembled by simple hand movements. The unpreserved drug which is in danger of contamination in the presence of air is securely stored in the reservoir which is sterilely sealed until directly before administering, such that the drug can be stored in this state for a period of several days or for that matter even months or years. The sterility is maintained until directly before the drug is used by the patient or an administering physician.

In some embodiments, an administering device in accordance with the present invention comprises a sequence controller and a reservoir which is sterilely sealed and contains a liquid drug in the form of, for example, a liquid formulation of FSH or an FSH variant. The use of carpoules or syringes which contain an unpreserved drug, for example FSH or an unpreserved FSH variant, in a sterile state and therefore non-perishable even without preservatives, is also a subject of the present invention. Within this aspect, the present invention also relates to an administering device which is incapable of dosing, i.e. which has no dosing member, although the option of individual dosing by the patient personally may be advantageous for administering such drugs. Other drugs which can be stored in accordance with the present invention in an unpreserved state in a sterilely sealed reservoir of the administering device and can thus be stored for a practically unlimited period of time in commercial circulation, with the physician or also even with the respective patient, are for example neuroleptic drugs (fluphenazine decanoate), vasodilative agents (epinephrine), blood products (etamsylate, epoetin alfa, filgrastim (G-CSF), nadroparin calcium, desmopressin acetate), drugs for treating rheumatic diseases (methotrexate, etanercept), oncological drugs (cladribine, human interferon gamma-lb ADN) and drugs for treating infectious diseases (herpes simplex type 1/type 2, human immunoglobin). Usual or preferred active agents for each group of drugs are given in brackets.

In some embodiments, an FSH-based drug contains an alpha subunit and a beta subunit. The proteins for the formulations which can be used can be obtained by various methods. The FSH which is to be used is a heterodimer comprising an α subunit and a β subunit, as described in more detail in EP 1 188 444 A1. In some embodiments, a formulation of FSH and/or an FSH variant in an aqueous solvent is administered using the device in accordance with the present invention. The expression "aqueous solvent" refers to a liquid solvent which contains water. Aqueous solvent systems can consist of water only or can consist of water and one or more miscible solvents and can contain other dissolved constituents (solutes) such as for example sugar or other inactive ingredients. The miscible solvents which are conventionally used are the short-chain organic alcohols such as methanol, ethanol, propanol, short-chain ketones such as acetone, and polyalcohols such as glycerin. The solvent system may consist only of water for injection purposes. Inactive ingredients can be selected from isotonicity agents, preservatives, buffer systems, in particular phosphate buffers, thioether compounds such as methionine as antioxidants, dispersants and/or emulsifiers such as poloxamers and mixtures of them. The formulation does not contain any preservatives, e.g. any preservative of the group consisting of phenol, m-cresol, chorocresol, a paraben selected from methylparaben, ethylparaben, propylparaben or butylparaben, benzalkonium chloride, benzethonium chloride, sodium dehydroacetate, benzyl alcohol and thiomersal. It is also preferred if the formulation is free of polycarboxylic acids, oligocarboxylic acids and dicarboxylic acids and of glycine and/or glycerin.

For administering unpreserved liquid drugs, such as administering liquid formulations of FSH or an FSH variant, it may be advantageous if only a drug quantity which is at most as large as a daily dosage is stored in the sterilely sealed reservoir, e.g. at most as large as a maximum dosage (single dosage) in which the drug in question is administered in a single administration of a few minutes' duration at most, e.g. a single injection. The reservoir and therefore also the administering device may be therefore a reservoir and an administering device for a single dosage of the drug. The maximum dosage for drugs based on, for example, FSH or an FSH variant is typically 300 IU, in exceptional cases 500 IU, as measured over a multitude of patients. In the case of such a drug, the drug quantity situated in the reservoir therefore corresponds to a dosage of 500 IU at most, or 300 IU at most, in some preferred embodiments. Since a majority of patients may only require lower dosages for each individual administration, for example 200 IU at most or even only 100 IU at most, the content amount in such a therapy may correspond at most to this dosage.

In a further development of the present invention, administering devices supplied to patients each may comprise a reservoir which comprises a content amount which is precisely adapted to the actual requirement of the respective patient. Administering devices which are identical in design can then, for example, be used in two, three or more different content-amount variants. In the case of an FSH-based therapy, for example, administering devices can be supplied which are identical in design and differ from each other substantially only with regard to the content amount of their reservoir, for example one device comprising a reservoir which contains 300 IU of the drug, another device comprising a reservoir which contains 200 IU of the same drug, and another device comprising a reservoir which contains 100 IU of the drug, each in a sterile state. Another subdivision into intermediate increments is also possible, for example in the form of a fourth content-amount variant comprising a reservoir which contains 150 IU of the drug in a sterile state. The device for administration may be designed for single use as a disposable item in each case and may advantageously be disposed of with the household waste. Not until immediately before administering is the drug in the reservoir—which is sterilely sealed up until this point in time—brought into contact with the outside environment.

Two variants can be considered for the sterile seal on the reservoir. In the first variant, the reservoir is formed by a carpoule or ampoule which comprises an outlet for administering which is sterilely sealed by a septum which can be pierced. In such embodiments, the drug is sterilely enclosed between the septum and a piston which can be axially moved. Such a reservoir is used together with a needle unit comprising a needle holder and an injection needle which protrudes through the needle holder. The needle holder serves to hold the injection needle and to establish the fluid connection between the needle and the reservoir. For the connection, the reservoir itself or the housing can comprise a connecting portion in the region of the outlet of the reservoir. The connecting portion and a connecting portion of the needle holder are designed to co-operate, such that when the mechanical connection between the needle holder and the connecting portion of the reservoir or housing is established, the injection needle pierces the septum. Once the septum has been pierced, the interior space of the reservoir is connected to the environment via the needle. Once this fluid connection has been established, the drug is administered with as little delay as possible. The administering device or at least a part of the device which contains the completely or partially emptied reservoir, or as applicable the reservoir only, is then disposed of. In the second variant, a syringe or syringe-like structure forms the reservoir. As opposed to the first variant, the reservoir of the second variant already comprises an injection needle at its distal end, such that the fluid connection between the reservoir and a downstream outlet of the injection needle already inherently exists. The sterile seal is ensured by an external sealing element which sterilely seals the needle outlet. The sealing element is removed directly before use.

In one embodiment, in which the drug is, for example, already contained in the reservoir in exactly the dosage which is to be delivered by a single administration, it is possible to omit the feature of the ability to dose or select the amount of the drug to be administered; correspondingly, the dosing member can be omitted. It may be also advantageous in such embodiments if the administering device features a priming function. The priming function can be fulfilled by the conveying member, by blocking or locking it in a releasable blocking engagement in the initial state of the administering device, wherein it has to be moved out of said engagement by applying a force or torque. The short priming stroke expels a volume from the reservoir which is predetermined by the length of the priming stroke. The end of the priming stroke may be defined by a priming abutment. In contact with the priming abutment, the conveying member can then perform the delivery movement. The delivery movement may be an axial movement in an advancing direction. The priming stroke may likewise be an axial movement in the advancing direction. Between the priming stroke and the delivery stroke, a transverse movement of the conveying member may be required and also may be only possible once the priming stroke has been performed, thus securely separating priming and delivery from each other.

Even in therapies using an unpreserved drug or a reservoir filled for a single administration only, i.e. a single dosage, it may be advantageous if the administering device features the ability to dose the drug, i.e. comprises the aforementioned dosing member. In this way, despite an optional variety of variants with regard to the content amount for a respective single administration only, it is possible to set the dosage even more precisely in each variant. In other words, by providing a plurality of content-amount variants, it is possible to reduce the drug quantity as considered over a large number of patients as a whole, i.e. as compared to embodiments in which the reservoir respectively contains the maximum dosage which is ever delivered in a single administration within the therapy. Conversely, the individual patient can even more individually set, within the suitably selected content-amount variant, the dosage tailored to them and administer this dosage.

In some preferred embodiments comprising the ability to select or set the dosage, it may also be preferred if priming and then delivering the dosage set are movements in the same direction, e.g. axial movements in the advancing direction of a piston which displaces the drug. In the initial state, a dosing blocking or locking engagement prevents dosing movements of the dosing member but enables the priming stroke at the end of which the dosing member moves out of the dosing blocking engagement and into a pressing contact, e.g. an axial pressing contact, against a priming abutment. Once the priming stroke has been performed, and/or when the dosing member is in contact with the priming abutment, the dosing member can be moved transverse to the direction of the priming movement, to be able to set the desired dosage. In some preferred embodiments, the dosing member and the conveying member are fixedly connected to each other in relation to the direction of the priming stroke, for example formed in one piece. If, in alternative embodiments, the two members should be able to be moved relative to each other in this respect, then either the dosing member or the conveying member can move into abutting contact with the priming abutment.

In some preferred embodiments, a retaining element is provided which moves the conveying member, in the course of its delivery movement, into a retaining engagement which blocks or at least impedes a movement of the conveying member counter to the advancing direction. While a block or lock is preferred in some embodiments, a releasable retaining engagement may be advantageous. To move into the retaining engagement, the conveying member is moved over and past the retaining element during its delivery movement, such that an audible or tangible clicking sound is generated. In some embodiments, the retaining element and a corresponding engaging counter element of the conveying member are arranged relative to each other such that the retaining engagement is automatically initiated only at the end of the delivery movement, such that the fact that delivery has been completed is audibly or tangibly signaled to the patient. To keep the manufacturing costs of the administering devices, including those which allow the dosage to be set, as low as possible, in some embodiments the present invention provides for realizing the housing and the functions of priming and conveying and, if realized, dosing using a total of only two or three separately formed parts. If the reservoir is a container accommodated in the housing, e.g. a carpoule, ampoule or vial, then the container is additional, together with a piston which seals the container. These parts can be molded from plastic by injection-molding, wherein an accommodated container can also be produced from glass. The housing comprising the dosing member can thus alone already fulfill the dosing functions of the administering device; thus, the dosing member and the housing alone already form a complete dosing means. In the initial state, the housing can also be in the dosing blocking engagement with the dosing member and/or can directly form the rotational abutment of some preferred embodiments. An activating element which, when activated, triggers the delivery can be formed in one piece with the conveying member. The same activating element can also be formed in one piece with the dosing member and form its operating area for dosage setting. If the conveying member is produced separately from the dosing member, the two parts may be joined, axially or rotationally fixed, to each other when the device is assembled. (The word "or" is used here, as elsewhere, in its usual logical sense of "inclusive or", i.e. it encompasses both the meaning of "either . . . or" and the meaning of "and", unless only one of these meanings can exclusively follow from the respectively specific context.) In relation to producing the dosing member and the conveying member as separate parts, this means that the conveying member and the dosing member are either joined to each other such that they cannot be axially moved relative to each other or are joined to each other such that they cannot be rotationally moved relative to each other or, as may be preferred in some embodiments, are joined to each other such that they cannot be axially or rotationally moved relative to each other. In one preferred modification, a dosing and conveying member which is formed in a single piece forms a piston rod, at least one dosing element required for selecting the dosage, a delivery abutment which limits the delivery stroke and an operating element for selecting the dosage or activating for delivery. Such a dosing and conveying member also forms a priming abutment for limiting the priming stroke. Of the three molded elements mentioned, i.e. the dosing element, the delivery abutment and the priming abutment, two or all three can be formed by the same molded element. The dosing blocking element can likewise be formed in one piece on the dosing and conveying member, as can an optional dosing latching element or dosing latching structure for setting the dosage in discrete increments. In some preferred modifications, the dosing blocking element or dosing latching element or dosing latching structure can also be formed separately from the dosing and conveying member, which comprises the remaining functions mentioned, and can be joined to it, e.g. fixedly, i.e. such that it cannot be translationally and rotationally moved.

An administering device which allows the dosage to be set may feature a dosage display comprising a dosage scale and a marker which displays the dosage set by its position relative to the dosage scale. The marker can be formed by a window in a shell portion of the housing, through which the dosage scale can be read. The dosage scale can be formed on an outer circumferential area of the dosing member which passes below the window when the dosage is set. Instead of forming a window in the housing, the housing can also be produced—in areas or as a whole—from a transparent or translucent material and comprise a marker in the form of an imprint or a projecting molded element.

In a further development of the present invention, such a dosage display can form the abutment, e.g. a rotational abutment, for blocking or locking the dosing member in the dosing blocking engagement. The dosing blocking abutment can be formed by a side wall of the window or by a marker shaped as a projection. The same window can also form an additional abutment, namely an abutment which the dosing member has to overcome in the direction of the priming movement to move out of the dosing blocking engagement. This optional additional abutment may have to be overcome against an elastic restoring force, wherein the restoring force points transverse to the direction of the priming movement. The restoring force can be provided by an elastic snapper, a bending tongue formed on the dosing member. In a reversal of the arrangement, such a snapper can also be formed on the housing. An elastic snapper of the dosing member and an elastic counter snapper of the housing can also as applicable co-operate in the manner described, to releasably hold the dosing member in the dosing blocking engagement.

DETAILED DESCRIPTION

With regard to fastening, mounting, attaching or connecting components of the present invention, unless specifically described as otherwise, suitable mechanical fasteners and methods may be used. Other appropriate fastening or attachment methods include adhesives, welding and soldering, the latter particularly with regard to the electrical system(s) of the invention, if any. Suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

Figure 1:
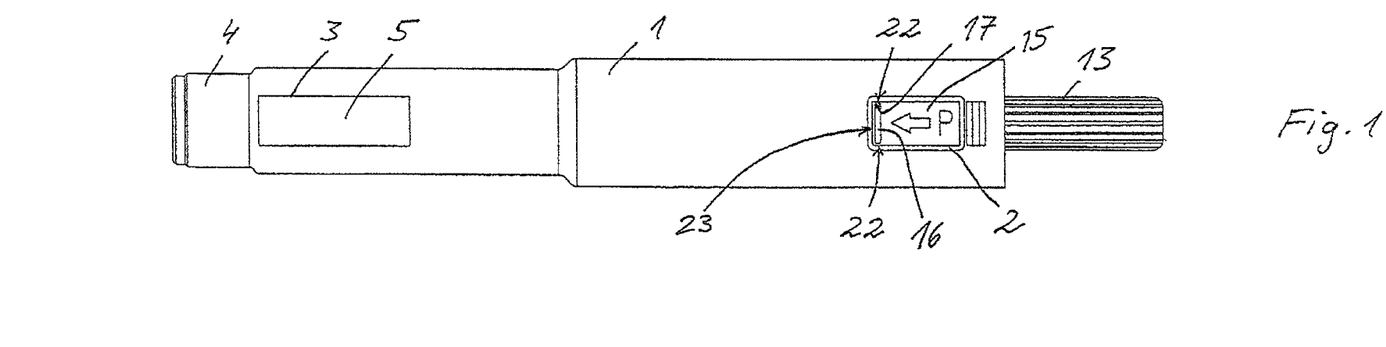
FIG. 1 depicts an embodiment of an administering device in accordance with the present invention in an initial state before priming.
Figure 2:
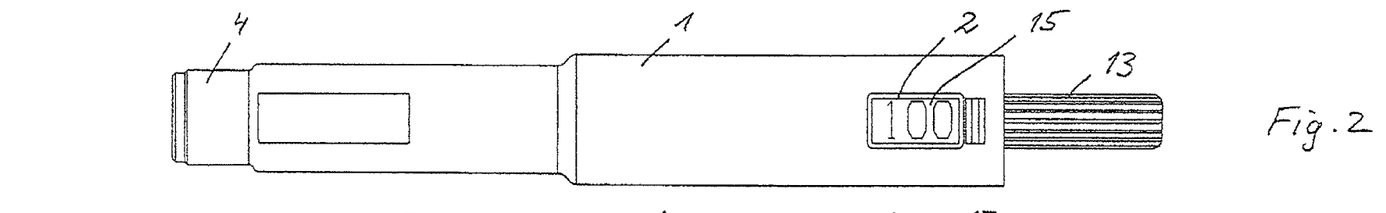
FIG. 2 shows the administering device of FIG. 1 after priming and setting a dosage.
Figure 3:
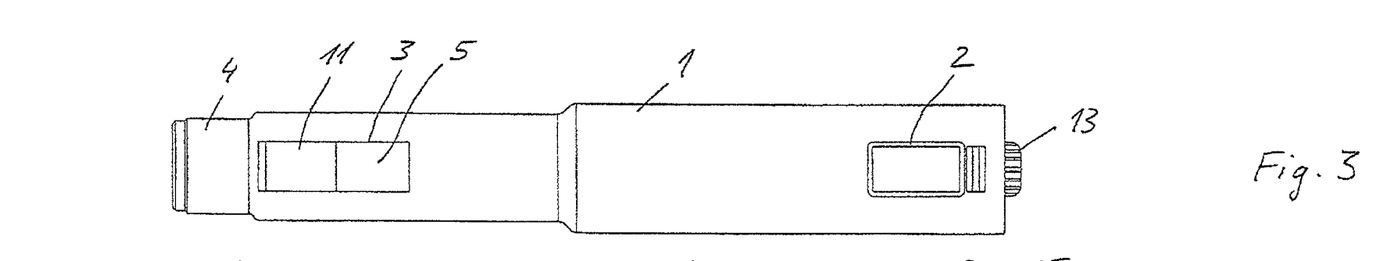
FIG. 3 shows the administering device after delivering the dosage set.

FIGS. 1 to 3 each show the same lateral view of an administering device of a first exemplary embodiment of the present invention. The administering device is an elongated injection pen. The administering device is designed for single use, for a single injection of a liquid drug which can be a liquid formulation based on FSH and or an FSH variant for a hormone treatment for stimulating the ovaries and consequently, by fertilizing the stimulated egg cells, pregnancy. The liquid drug, i.e. the liquid formulation, is unpreserved, i.e. does not contain any preservatives. If, as may be preferred, the drug is a formulation which contains FSH and or an FSH variant, it therefore has to be administered within a few minutes, at any rate within a few hours, after contact with the ambient air.

FIG. 1 shows the administering device in an initial state before use. The patient is provided with the device in this state. The device comprises a sleeve-shaped housing 1, comprising a front, distal housing portion in which a reservoir 5 is accommodated which contains the drug in a sterile state, and a rear, proximal housing portion in which structures are formed which co-operate with a dosing and conveying mechanism or means of the device, to enable the patient to individually select a dosage of the drug to be administered. The proximal housing portion can also serve as a gripping part of the device. An operating element 13 of the dosing and conveying means, which protrudes out of the housing 1 in the proximal (rearward) direction at the proximal end, can be seen.

A dosage display window 2 and a reservoir window 3 are formed in the housing 1. The dosage set can be read through the window 2, and the reservoir 5 can be seen through the window 3. The distal end of the housing 1 comprises a connecting portion 4 to which a needle unit can be fastened. The needle unit is not fastened until immediately before administering, to ensure the sterility of the drug up until this point in time.

As mentioned, FIG. 1 shows the administering device in its initial state with the reservoir 5 sterilely sealed, more specifically in its storage state in which the device can be stored for a longer period of at least several months, since the airtight, sterile seal on the reservoir 5 ensures the non-perishability of drugs, including unpreserved drugs. to administer the drug, the patient connects a needle unit comprising an injection needle to the housing I, namely to its connecting portion 4, immediately before administering. As the needle unit is connected, a proximal needle portion of the injection needle pieces a septum which sterilely seals an outlet of the reservoir 5 airtight. Once the septum has been pierced, the drug is connected to the environment via the injection needle and has to be administered within a short period of time, optimally immediately, if the drug is an unpreserved drug based on FSH or an FSH variant, as may be preferred.

In some embodiments, a patient or user can personally set a dose which she/he wishes to administer. The reservoir 5, which is filled by the manufacturer, contains a maximum dosage of the drug which is set such that, as considered over a larger group of potential patients, it is sufficient for each of said patients. Persons who only require a lower dosage for each administration can set this lower dosage themselves. Once used, the device is disposed of together with the residual amount of the drug which correspondingly still remains in the reservoir 5. The device also features the ability of priming, i.e. of venting of reservoir 5. Priming displaces any free gas which may be contained in the reservoir 5, e.g. nitrogen or air, out of the reservoir 5. Air can enter the reservoir 5 during manufacture when filling the reservoir 5 or when connecting the injection needle 7. On the one hand, this air or other gas as applicable should not be administered; on the other hand, however, it also distorts the dosage, since the administered dosage would deviate from the dosage set by the amount of gas which without priming is situated in the reservoir 5.

The administering device comprises a conveying means or arrangement 10 comprising a first conveying member 11 and a second conveying member 12. The first conveying member 11 is a piston 11 which is accommodated such that it can be moved within the reservoir 5 and which sterilely seals the reservoir 5 at one end and can be moved within the reservoir 5 in an advancing direction along a central longitudinal axis A of the device toward the outlet. The injection needle 7 likewise extends axially on the axis A. The second conveying member 12 forms a piston rod. The conveying member 12 is only in an axial pressing contact with the piston 11, i.e. when the device is activated, the conveying member 12 presses the piston 11 in a loose pressing contact axially toward the outlet of the reservoir 5.

The conveying member 12 also forms a dosing mechanism or means together with the housing 1. The conveying member 12 may therefore be referred to in the following as the dosing and conveying member 12. To fulfill the dosing function, the dosing and conveying member 12 can be rotationally moved relative to the housing 1 about the axis A, i.e. when the dosage is being set, the dosing and conveying member 12 performs a rotational dosing movement about the axis A. To fulfill the conveying function, it can be translationally moved along the axis A in the advancing direction. A proximal end portion of the dosing and conveying member 12 also forms the activating element 13. The patient sets the dosage on the activating element 13 and initiates the delivery movement of the dosing and conveying member 12 by exerting a pressure force in the advancing direction. To fulfill the different functions, i.e. priming, dosing and conveying and/or delivery, the dosing and conveying member 12 comprises a plurality of structural elements, e.g. a first dosing element 14 for dosing which simultaneously also forms a delivery abutment and thus itself fulfils both a dosing function and a delivery function. A dosing blocking element 16 is another of these structural elements.

When the dosage is being set, the first dosing element 14 co-operates with a plurality of second dosing elements 24 which are arranged in a distribution about the longitudinal axis A and formed in a dosing portion 1a of the housing 1 on its inner surface area. The dosing elements 24, which can comprise any selected number of such elements, are axial guides for the first dosing element 14 which co-operates as an engaging element with said guides 24. The dosing elements and/or guides 24 exhibit different axial lengths, wherein these lengths each correspond to a dosage which can be set. The dosing elements 24 are, for example, formed as axial blind grooves on the inner circumference of the dosing portion 1a. The blind grooves are open at their proximal ends, such that the first dosing element 14 can move in the advancing direction into one of these grooves 24 in accordance with the rotational angular position of the dosing and conveying member 12 and can be moved in the advancing direction in the course of a delivery stroke in the groove 24 in question, up to its distal end. As already mentioned, the dosing element 14 forms a delivery abutment in a dual function by moving into axial abutting contact against a delivery abutment 21 of the housing 1, formed in the example by the distal end of the respective blind groove 24. The length of the delivery stroke thus corresponds to the length of the dosing element 24 which co-operates with the dosing element 14 in accordance with the dosage set.

The dosing and conveying member 12 forms a dosing latching or locking means with the housing 1. A dosing latching structure 19 which extends around the rotational axis A is formed on an outer circumference of the dosing and conveying member 12 for this purpose. When the dosing and conveying member 12 is rotationally moved, an elastically flexible dosing latching element 29 in the form of a radially flexible snapper which is formed on the housing 1 slides over the dosing latching structure 19. The dosing latching structure 19 is formed in the manner of an outer texture, teeth or an outer toothing which is, for example, formed directly on the outer surface area of the dosing and conveying member 12, e.g. circumferentially about the axis A, and corresponds in its separation to the separation of the second dosing elements 24, such that the dosing latching element 29 respectively engages with a recess of the dosing latching structure 19 when the dosing element 14 is exactly axially flush with one of the dosing elements 24. In a reversal of the arrangement, a dosing latching or locking structure could also be formed on the inner surface area of the housing 1 and an elastically flexible dosing latching element could be formed on the dosing and conveying member 12.

In the exemplary embodiment, all the functional and/or structural elements are formed either on the housing 1 or on the dosing and conveying member 12. In another preferred modification, the dosing blocking element 16 and the dosing latching structure 19 can be formed separately from the rest of the dosing and conveying member 12, e.g. on a sleeve part corresponding to the sleeve part of the exemplary embodiment, which forms the outer circumference mentioned in the paragraph above. Such a separately formed sleeve part comprising the dosing blocking element 16 and the dosing latching structure 19 would however be fixedly joined, such that it cannot be moved, to the part of the dosing and conveying member 12 which protrudes through the housing 1 and forms the piston rod. As a result, a joined dosing and conveying member 12 would be obtained which in terms of its shape would correspond to that of the exemplary embodiment.

In the initial state of the administering device (FIGS. 1 and 4), the dosing and conveying member 12 is situated in a dosing blocking engagement in which it is prevented from being rotationally moved about the axis A. The dosing blocking engagement is effected by the dosing blocking element 16 which is likewise formed on the dosing and conveying member 12. The dosing blocking element 16 is in the dosing blocking engagement with the housing 1. For this purpose, the housing 1 forms a rotational abutment 22 as a blocking counter element. The dosing blocking engagement is formed such that the dosing blocking element 16 protrudes into the dosage display window 2 in the initial state in which the dosing and conveying member 12 adopts its rearmost position, in relation to the advancing direction, relative to the housing 1 and the reservoir 5, such that the left-hand and right-hand side wall of the dosage display window 2 each act as a rotational abutment 22 clockwise and anti-clockwise about the axis A.

Figure 7:
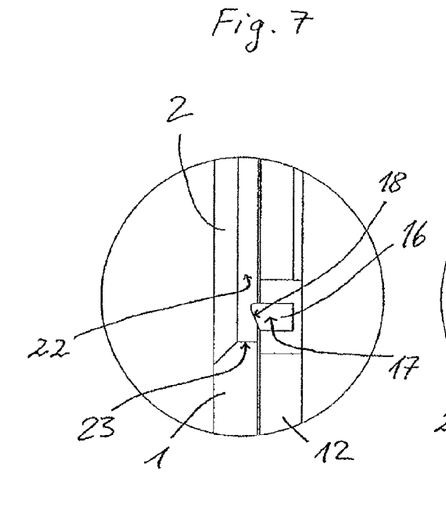
FIG. 7 is a detail of FIG. 4, depicting a dosing blocking engagement of a dosing member of the administering device.

FIG. 7 shows an enlarged detail of the region in which the dosing blocking engagement exists in the initial state of the device. The dosing blocking element 16 protrudes radially outward over an outer circumferential area of the dosing and conveying member 12, into the dosage display window 2. It is arranged on the dosing and conveying member 12 such that it protrudes into the window 2, immediately behind a front facing wall 23 of the window 2 in relation to the advancing direction, and thus lies axially opposite said facing wall 23. For the dosing blocking engagement, which in this exemplary embodiment is formed as a rotational blocking engagement due to the rotational dosing mobility of the dosing and conveying member 12, the dosing blocking element 16 exhibits a width in the circumferential direction about the axis A—the rotational axis of the dosing and conveying member 12—which is such that it almost completely fills the window 2 in the circumferential direction, as can be seen in FIG. 1, i.e. it does not have any "breathing space" in the circumferential direction in the dosing blocking engagement and lies opposite the rotational abutments 22 formed by the two side walls of the window 2 in a virtually tight fit in both rotational directions. The abutment areas of the dosing blocking element 16 which act in the two rotational directions of the rotational mobility are provided with the reference indicator 17.

In addition to the two rotational abutment areas 17, the dosing blocking element 16 comprises an axial guiding area 18 which is inclined in relation to the axis A and co-operates with the facing area 23 of the dosage display window 2 which lies axially opposite it. If a sufficiently large axial pressure force is exerted on the dosing and conveying member 12, namely by pressing on the operating element 13, the inclined guiding area 18 of the dosing blocking member 16 is pressed axially against the facing area 23. The dosing blocking member 16 is elastically flexible radially in relation to the axis A, such that it slides off on the facing area 23 due to the inclined guiding area 18, wherein it moves radially inward and thus out of the dosing blocking engagement with the left-hand and right-hand rotational abutment 22 in relation to the rotational direction. The facing area 23 forms an unblocking abutment 23.

Figure 8:
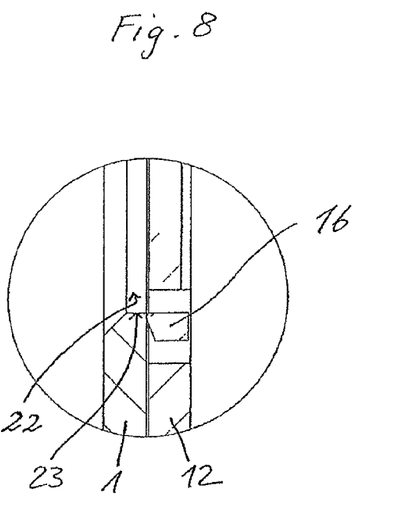
FIG. 8 is a detail of FIG. 5, showing the dosing member which has moved out of the dosing blocking engagement.

FIG. 8 shows the state in which the dosing blocking element 16 has just passed the unblocking abutment 23 in the advancing direction, such that the dosing and conveying member 12 is free of the dosing blocking engagement and can be rotationally moved about the axis A.

Figure 6:
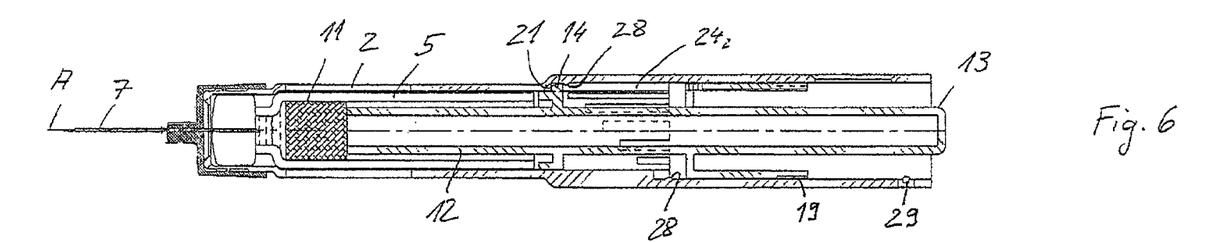
FIG. 6 is a longitudinal section of the administering device after delivery.
Figures 9, 10:
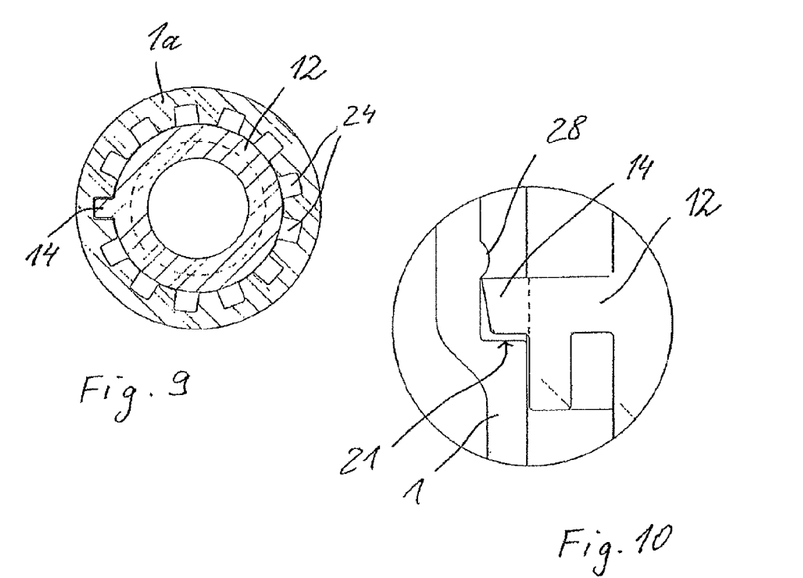
FIG. 9 shows a dosing portion of the administering device in a cross-section.
FIG. 10 is a detail of FIG. 6, showing the dosing member which is situated in a retaining engagement.

FIG. 9 shows the administering device in a cross-section in the region of the dosing portion 1a, during delivery of the drug. The dosing element 14 is axially guided by one of the dosing elements 24 formed uniformly around the axis A in the dosing portion 1a, such that during its delivery stroke, the dosing and conveying member 12 maintains the rotational angular position set when selecting the dosage. FIGS. 6 and 10 show the administering device after the dosage set has been completely delivered, for example after a maximum dosage has been delivered.

Figure 4:
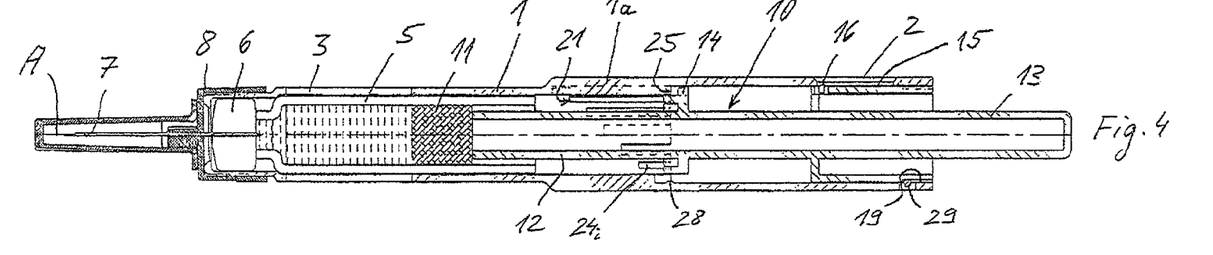
FIG. 4 is a longitudinal section of the administering device in its initial state.
Figure 5:
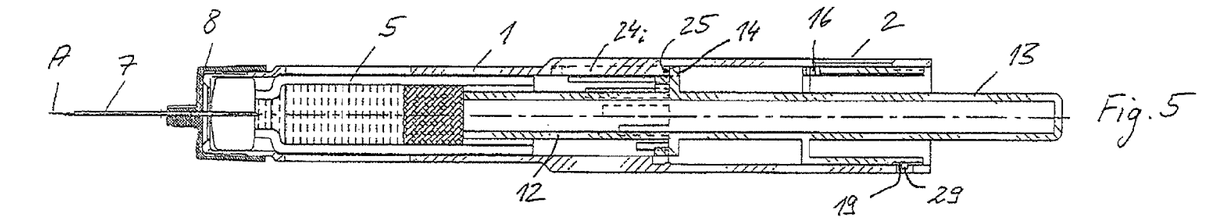
FIG. 5 is a longitudinal section of the administering device after priming.

FIG. 6 shows the administering device in a longitudinal section which is offset from the longitudinal sections of FIGS. 4 and 5 by a few angular degrees about the axis A. The axially longest of the dosing elements 24 is hidden in FIGS. 4 and 5, while the longitudinal section of FIG. 6 extends through said dosing element 24. The delivery stroke is terminated by the respective delivery abutment 21 at the front end of each of the dosing elements 24 in the advancing direction, in that the dosing element 14 abuts against the respective delivery abutment 21 of the housing 1 in the advancing direction, as shown by FIG. 6. Each of the dosing elements 24 comprises a delivery abutment 21 at its front end in the advancing direction, wherein the delivery abutments 21 are formed at different axial levels corresponding to the different dosages.

Another feature which the administering device exhibits is a retaining means for the dosing and conveying member 12. The retaining means ensures that the dosing and conveying member 12, once it has completely performed the delivery stroke, remains in the delivery position which it has then adopted. The retaining means comprises retaining elements 28 which are assigned to the dosing elements 24, i.e., one of the retaining elements 28 for each one of the dosing elements 24, respectively. The retaining element 28 of the axially longest dosing element 24 and the retaining element 28 of the axially shortest dosing element 24 can be seen in FIG. 6. The retaining elements 28 are formed by the housing 1 and are, for example, formed on its inner surface area as retaining cams which protrude radially inward. The delivery abutment 14 or dosing element 14, respectively, is inclined in relation to the axis A on a front side which points in the advancing direction, such that it can slide over the retaining element 28 of the respective dosing element 24 in the advancing direction. The rear side of the delivery abutment 14 or dosing element 14, respectively, points at least substantially orthogonally with respect to the axis A, such that in co-operation with the respective retaining element 28, it holds the dosing and conveying member 12 in the latter's delivery position, either blocking it against moving counter to the advancing direction or at least impeding such a retracting movement. This helps ensures the administering device cannot be inadvertently and improperly used for another delivery, if the dosage set was smaller than the drug dosage situated in the reservoir 5 in the initial state.

The functionality of an administering device in accord with the present invention is explained below in context. The patient is provided with the device in the initial state of FIG. 1. For administering, the patient connects the injection needle 7 to the reservoir 5 by plugging or screwing the needle 5 holder 8 onto the connecting portion 4. This state is shown in FIG. 4. The patient then merely has to remove the needle cap which in FIG. 4 covers the injection needle 7.

The reservoir 5 is vented before administering. The administering device forces this priming step, since the dosage to be administered cannot be set until after priming. The volume which is expelled during priming is predetermined, namely by the axial clear distance which the delivery abutment 14 exhibits from the priming abutment 25. Prematurely setting the dosage is prevented by the dosing blocking engagement between the dosing blocking element 16 and the rotational abutment 22 of the housing 1. The dosing blocking engagement between 16 and 22 can also be seen in FIG. 1.

In the initial state, the dosage display indicates to the patient that priming has to be performed and how this is done. The display which can be seen in FIG. 1—a pictogram of a directional arrow pointing in the advancing direction and a "P" for "priming"—appears in the dosage display window 2. The patient vents the reservoir 5 by exerting an axial pressure force on the operating element 13. The elastically flexible dosing blocking element 16 yields radially inwardly under the pressure force, in that its guiding area 18 slides over the unblocking abutment 23 of the housing 1, whereby the dosing blocking element 16 is moved radially inward, out of the dosing blocking engagement. The process can be seen from FIGS. 7 and 8. The priming stroke is limited by the priming abutment 25, i.e. the priming stroke is terminated as soon as the delivery abutment 14 abuts against the priming abutment 25.

FIG. 5 shows the administering device directly after the priming stroke has been performed. The dosing blocking engagement has been released. In this state, the dosage to be administered can be set by rotating the dosing and conveying member 12 about the axis A into a rotational angular position in which the delivery abutment 14, which acts as a dosing element 14 during dosing, is axially flush with the dosing element 24 which in terms of its axial length corresponds to the dosage to be administered. The dosage set can be read in the dosage display window 2 (FIG. 2).

Once the dosage has been set, the patient places the administering device comprising the injection needle 7 at the desired injection point and injects the injection needle 7 into and under the skin. Once the injection needle 7 has been injected, the patient delivers the dosage set by exerting an axial pressure force on the operating element 13 and so moving the dosing and conveying member 12 in the advancing direction, wherein the dosing and conveying member 12 presses against the piston 11 and advances it within the reservoir 5 toward the outlet until the delivery abutment 14 of the dosing and conveying member 12 abuts against the delivery abutment 21 assigned to the selected dosing element 24. The delivery stroke of the dosing and conveying member 12 and the piston 11, i.e. the conveying means 10, corresponds to the axial length of the selected dosing element 24. FIG. 9 shows the administering device in a cross-section during the delivery stroke, with the dosing element 14 and/or delivery abutment 14 in guiding engagement with the selected dosing element 24.

Shortly before the end of the delivery stroke, the delivery abutment (dosing element) 14 passes over the retaining element 28 assigned to the selected dosing element 24. The clicking sound thus generated provides the patient with an audible and also tangible signal to the effect that the delivery stroke has been completely performed. FIGS. 6 and 10 show the administering device after the delivery stroke has been completely performed; FIG. 10 shows an enlarged detail of the region around the retaining element 28. The dosing and conveying member 12 is then situated in the retaining engagement which prevents the dosing and conveying member 12 from retracting counter to the advancing direction or at least significantly impedes it. As can be seen in FIG. 3, the dosage display provides a blind display through the window 2. In a further development, the dosage display 15 can be amended to include a pictogram or color marking or even text to provide the patient with a positive content feedback that the dosage set has been completely delivered. The patient can see the piston 11 through the reservoir window 3. As a result, this also visually signals to the patient that the delivery has been completely performed.

Figures 11, 12:
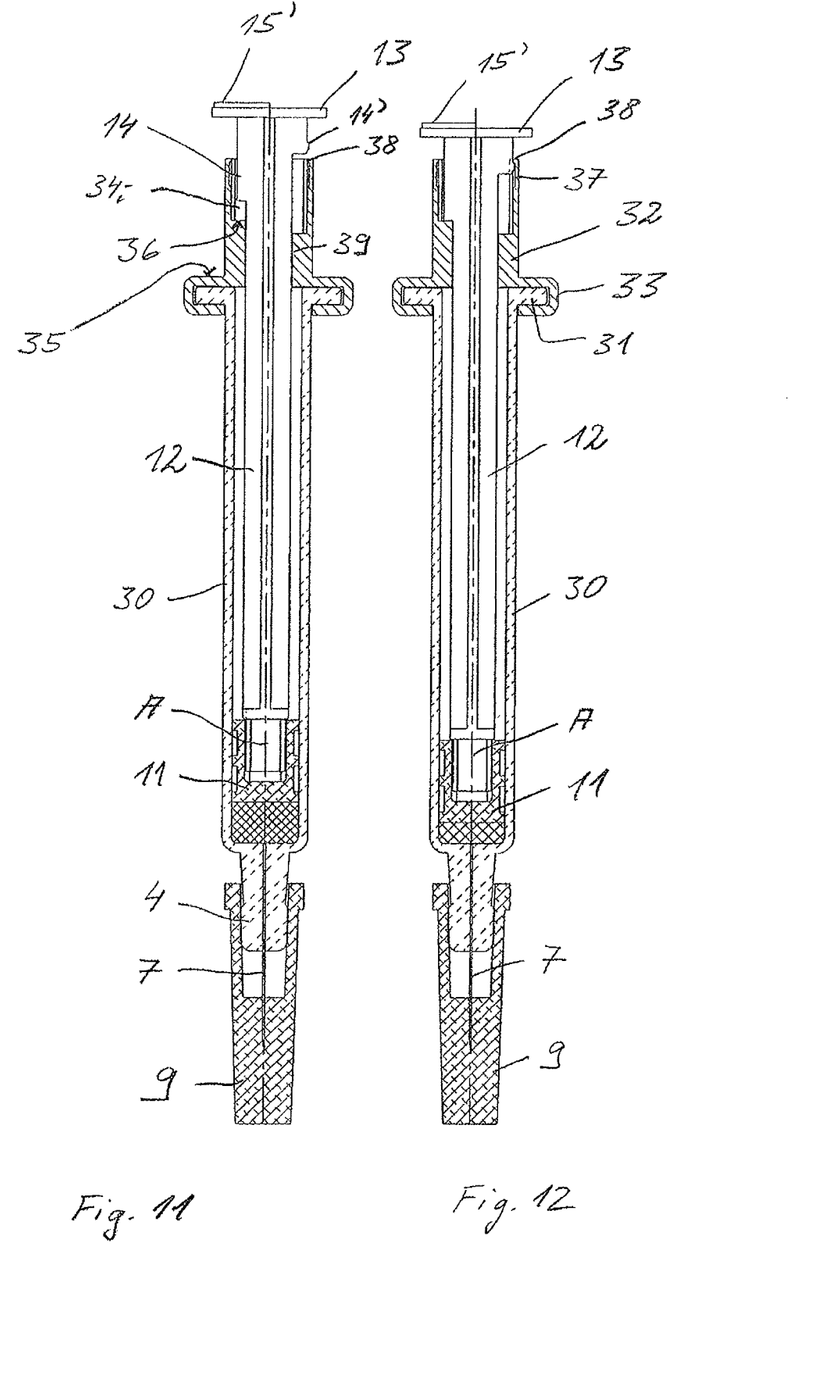
FIG. 11 depicts another embodiment of an administering device in accordance with the present invention in an initial state.
FIG. 12 shows the administering device of FIG. 11 after an administering procedure.

FIGS. 11 and 12 each show an administering device of another exemplary embodiment in a longitudinal section. FIG. 11 shows the device before administering, and FIG. 12 shows the device after administering. The administering device of this embodiment is designed for a single administration only.

The administering device of the second exemplary embodiment is shown in a content-amount variant in which the reservoir 30 contains a significantly smaller content amount of the drug in its sterilely sealed state—the initial state of the device—than would correspond to the maximum content amount. The device nonetheless features the ability to select the dosage. The patient can at most administer the predetermined content amount, possibly less a residue of liquid which cannot be displaced. The patient can however also set and administer a dosage which is smaller than the predetermined content amount.

The reservoir 30 is a syringe. At its outlet, it comprises the injection needle 7 which is fixedly connected to the syringe body. To sterilely seal the outlet end, an external sealing element 9 which sterilely encloses the outlet of the injection needle 7 airtight is placed onto a connecting portion 4 of the reservoir 30. At the proximal end, a piston 11 again sterilely seals the volume of the reservoir 30, filled with the liquid drug, airtight. The piston 11 of the second exemplary embodiment is also a simple stopper which however is connected to the dosing and conveying member 12 in a positive fit on its rear side. The drug can be a liquid, unpreserved formulation based on FSH or an FSH variant for a hormone treatment for stimulating the ovaries and consequently, by fertilizing the stimulated egg cells, pregnancy. The administering device can however, like that of the first exemplary embodiment, also be used in other therapies for administering other drugs. Some other preferred areas of use or application are mentioned herein above.

In the second exemplary embodiment, the housing is in two parts and comprises the reservoir 30 which is provided as a syringe and a proximal housing portion 32 which is placed onto the proximal end of the reservoir 30. The proximal end of the reservoir 30 comprises a connecting flange 31 which projects outwardly from the cylindrical main body of the reservoir 30 and onto which the housing portion 32 is slid from the side via its connecting structure 33 and held in its slid-on state on the reservoir 30 in a positive fit and a frictional fit. In the initial state of the device, which is shown in FIG. 11, the housing portion 32 mounts the dosing and conveying member 12 such that it can be axially moved in the advancing direction and rotationally moved about the axis A. The rotational mobility may be required for setting the dosage.

The dosing and conveying member 12 comprises a first dosing element 14 which co-operates with second dosing elements 34 for setting the dosage. As in the first exemplary embodiment, the dosing elements 34 are formed as axial guides of different lengths, e.g. as blind grooves, in the inner surface of the housing portion 32. As in the first exemplary embodiment, each of the dosing elements 34 is assigned a delivery abutment which in the second exemplary embodiment is provided with the reference sign 36, i.e. one delivery abutment 36 for each dosing element 34, formed by the axial end of the respective blind groove. During dosing, the dosing element 14 co-operates with the dosing elements 34 in the same way as the dosing element 14 of the first exemplary embodiment co-operates with the dosing elements 24.

As in the first exemplary embodiment, the dosing and conveying member 12 simultaneously also forms the operating element 13 for both setting the dosage and exerting the axial pressure required for delivery. The dosage set is displayed in the interaction between a dosage scale 35 and a marker 15'. The dosage scale 35 is formed on the outside of a rear side of the connecting structure 33 of the housing portion 32, around the axis A. The marker 15' is provided on the operating element 13. The operating element 13 is transparent, such that the patient can read the dosage on the dosage scale 35 from the rear through the operating element 13 on the basis of the rotational angular position of the marker 15'.

Once the dosage set has been completely delivered, the dosing and conveying member 12 moves into a retaining engagement with the housing portion 32, as in the first exemplary embodiment. The housing portion 32 comprises a retaining element 38 for this purpose. In FIG. 12, an additional retaining counter element 14' of the dosing and conveying member 12 grips behind the retaining element 38 to prevent the dosing and conveying member 12 from retracting after delivery.

In a modification of the dosing means, dosing elements 34 which form axial guides for the delivery abutment 14 or dosing element 14, respectively, are not formed on the housing portion 32. The delivery abutments 36, which are formed at axially different positions, are instead provided as steps circumferentially about the axis only. In such a modification, the delivery abutment 14 fulfils the abutment function and, only in connection with this, a dosing function. In the modification, the dosing and conveying member 12 is secured in a different way against a rotational movement out of the rotational angular position set when setting the dosage, namely by a rotational blocking structure 37 which only serves to prevent a relative rotational movement. In the modification, the dosing and conveying member 12 is rotationally secured, i.e. can no longer be rotated about the axis A relative to the housing portion 32, in its engagement with the rotational blocking structure 37 when 14' and 38 are in the retaining engagement.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. For example, it should be appreciated any feature, embodiment, structure, operation, method and/or component of the present invention may be implemented separately or in combination with any other feature, embodiment, structure, operation, method and/or component. All such modifications and variations are within the scope of the invention as determined by the appended claims when interpreted in accordance with the breadth they are fairly, legally, and equitably entitled.

The invention claimed is:

1. An administering device comprising:
   (a) a housing;
   (b) a reservoir for a liquid drug, the reservoir formed or accommodated by the housing;
   (c) a dosing member which can perform a dosing movement relative to the housing for setting a dosage of the drug to be administered; and
   (d) conveying means comprising a conveying member for delivering the dosage set,
   wherein in an initial state of the administering device, the dosing member is blocked in the direction of the dosing movement in a releasable dosing blocking engagement between a dosing blocking element of the dosing member and an abutment of the housing,
   wherein during a priming movement of the conveying member, the dosing member is moved in an advancing direction against an elastic restoring force of the dosing blocking element by a force acting in the advancing direction such that the dosing blocking element elastically flexes transverse to the advancing direction and overcomes the abutment of the housing to release the dosing blocking engagement,
   wherein the dosing member is rotatable about a rotational axis for performing the dosing movement relative to the housing when released from the dosing blocking engagement,
   wherein the conveying member is axially moved relative to the reservoir in the advancing direction for delivering the dosage set,
   wherein the conveying member moves into a retaining engagement with a retaining element, which causes the conveying member to adopt a delivery position when the dosage set has been delivered, the retaining engagement blocking or at least obstructing a movement of the conveying member counter to the advancing direction, and
   wherein the conveying member is in an abutting contact with the retaining element counter to the advancing direction in the retaining engagement.

2. The administering device according to claim 1, wherein the dosing member can be axially moved along the rotational abutment out of the dosing blocking engagement with the rotational abutment.

3. The administering device according to claim 1, wherein the dosing member is coupled to the conveying member such that it is moved out of the dosing blocking engagement by the priming movement of the conveying member.

4. The administering device according to claim 3, wherein the dosing member is slaved in the priming movement of the conveying member.

5. The administering device according to claim 1, wherein the conveying member can be moved relative to the reservoir in an advancing direction for performing the priming movement and delivering the dosage set.

6. The administering device according to claim 1, wherein the conveying member can be axially moved relative to the reservoir in the advancing direction for performing the priming movement, and the conveying member moves into an abutting contact with a priming abutment at the end of the priming movement, wherein the priming abutment limits the priming movement and is an axial abutment against which the conveying member moves into the abutting contact in the advancing direction.

7. The administering device according to claim 6, wherein when the conveying member is situated in the abutting contact with the priming abutment, the dosing member can perform the dosing movement and can be rotationally moved relative to the housing about a rotational axis which extends in the advancing direction.

8. The administering device according to claim 1, wherein:
   (i) the dosing member co-operates with a dosing structure of the housing for selecting the dosage;
   (ii) one of the dosing member and the dosing structure comprises a first dosing element and the other comprises a plurality of second dosing elements in a distribution about the rotational axis;
   (iii) each of the second dosing elements corresponds to a dosage which differs from the dosage of each of the other second dosing elements;
   (iv) either the first dosing element is an engaging element and the second dosing elements are guides which extend axially, or the first dosing element is a guide which extends axially and the second dosing elements are engaging elements; and
   (v) setting the dosage moves the dosing member into a rotational angular position in which the first dosing element moves into a guiding engagement with the second dosing element which corresponds to the dosage set.

9. The administering device according to claim 8, further comprising an activating element for manually activating the dosing member or the conveying member.

10. The administering device according to claim 9, wherein the dosing member cannot be axially or rotationally moved relative to the conveying member and is forming in one piece with the conveying member.

11. The administering device according to claim 10, wherein the activating element cannot be axially or rotationally moved relative to the conveying member and is formed in one piece with the conveying member.

12. The administering device according to claim 10, wherein the activating element cannot be axially or rotationally moved relative to the dosing member and is formed in one piece with the dosing member.

13. The administering device according to claim 1, further comprising a dosage display comprising a dosage scale and a marker which displays the dosage set by its position relative to the dosage scale, wherein the dosing member comprises the dosage scale and the marker is formed as a window in a shell region of the housing.

14. The administering device according to claim 13, wherein the housing forms the rotational abutment, or a side wall of a window formed in the housing forms the rotational abutment or the marker is formed as a window in a shell region of the housing and a side wall of the window forms the rotational abutment.

15. The administering device according to claim 6, wherein the housing forms the priming abutment and the housing forms a delivery abutment against which the conveying member moves into abutting contact during delivery, as soon as the dosage set is delivered.

16. The administering device according to claim 1, wherein the housing forms the retaining element.

17. The administering device according to claim 1, wherein the reservoir is formed by a carpoule or by a syringe in which a liquid drug based on FSH or an FSH variant is contained, wherein the drug is unpreserved and the reservoir is sterilely sealed.

18. The administering device according to claim 17, wherein when the reservoir is sterilely sealed, the reservoir contains an amount of the drug which is at most as large as a maximum dosage in which the drug is administered in a single injection.

19. The administering device according to claim 18, wherein the administering device or a part of the administering device which contains or forms the reservoir is a disposable item for a single administration.

20. The administering device according to claim 17, wherein the conveying member performs a delivery movement which delivers the drug and automatically moves into a retaining engagement which prevents or at least impedes another delivery after a single complete administration in which all of the drug contained in the reservoir or the dosage set by said dosing member is delivered.

21. The administering device according to claim 1, further comprising an injection needle in fluid connection with the drug situated in the reservoir and sterilely sealed off from the outside environment by a sealing element.

22. The administering device according to claim 1, wherein a septum which can be pierced sterilely seals the reservoir airtight and the housing or the reservoir comprises a connecting portion for connecting an injection needle which when connected pierces the septum.

23. The administering device according to claim 1, wherein the reservoir is formed by a carpoule or a syringe in which a piston is accommodated such that it can be moved toward an outlet of the reservoir to deliver the drug.

* * * * *

UNITED STATES PATENT AND TRADEMARK OFFICE
CERTIFICATE OF CORRECTION

PATENT NO. : 9,867,948 B2
APPLICATION NO. : 13/335275
DATED : January 16, 2018
INVENTOR(S) : Anjan Selz et al.

Page 1 of 2

It is certified that error appears in the above-identified patent and that said Letters Patent is hereby corrected as shown below:

In the Drawings

Sheet 3; Figure 9 Dosing element 24 is missing "i" as shown on attached sheet

In the Claims

Column 18, Line 63 Claim 10 Line 3 "conveying member and is forming" should be -- conveying member and is formed --

Signed and Sealed this
Twenty-third Day of October, 2018

Andrei Iancu
*Director of the United States Patent and Trademark Office*

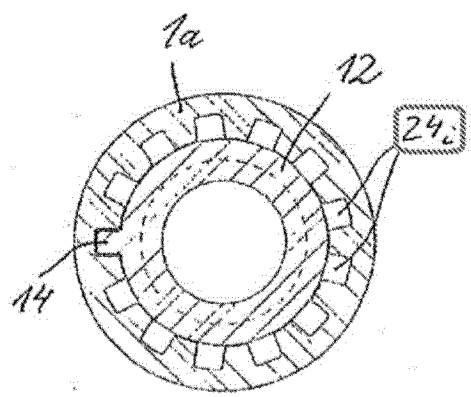
Fig. 9